United States Patent
Griffiths et al.

(10) Patent No.: US 12,263,113 B2
(45) Date of Patent: Apr. 1, 2025

(54) LIMB SUPPORT AND LIMB SUPPORT FASTENING ARRANGEMENT

(71) Applicant: FRONTIER THERAPEUTICS LIMITED, Blackwood (GB)

(72) Inventors: Phillip John Griffiths, Blackwood (GB); John Davies, Blackwood (GB)

(73) Assignee: Frontier Therapeutics Limited, Blackwood (GB)

( * ) Notice: Subject to any disclaimer, the term of this patent is extended or adjusted under 35 U.S.C. 154(b) by 259 days.

(21) Appl. No.: 15/554,780

(22) PCT Filed: Feb. 2, 2016

(86) PCT No.: PCT/GB2016/050228
§ 371 (c)(1),
(2) Date: Aug. 31, 2017

(87) PCT Pub. No.: WO2016/139445
PCT Pub. Date: Sep. 9, 2016

(65) Prior Publication Data
US 2018/0014963 A1    Jan. 18, 2018

(30) Foreign Application Priority Data
Mar. 3, 2015  (GB) .................................... 1503579

(51) Int. Cl.
*A61F 5/058*    (2006.01)
*A61F 5/01*    (2006.01)

(52) U.S. Cl.
CPC .......... *A61F 5/05816* (2013.01); *A61F 5/012* (2013.01)

(58) Field of Classification Search
CPC ........ A61F 5/05816; A61F 5/012; A61F 5/01; A61F 5/0111; A61F 5/0195; A61F 5/34;
(Continued)

(56) References Cited

U.S. PATENT DOCUMENTS 4,266,298 A * 5/1981 Graziano ................ A61F 5/012
2/22
5,085,214 A   2/1992 Barrett
(Continued)

FOREIGN PATENT DOCUMENTS

| EP | 2505167 A1 | 10/2012 |
|---|---|---|
| WO | 199911204 A1 | 3/1999 |
| WO | 2011135078 A1 | 11/2011 |

OTHER PUBLICATIONS

International Search Report and Written Opinion related to PCT/GB2016/050228, dated May 23, 2016, 10 pages.
(Continued)

*Primary Examiner* — Michelle J Lee
*Assistant Examiner* — Robin Han
(74) *Attorney, Agent, or Firm* — POLSINELLI PC

(57) ABSTRACT

A limb support fastening arrangement for fastening a limb support to a limb of a wearer is disclosed. The arrangement comprises a first and second fastening portion, the first portion comprising an inflatable chamber comprising an upper and lower chamber wall and a first fastener disposed proximate the upper chamber wall, the lower chamber wall being arranged in use, to extend proximate the limb of the wearer. The second portion similarly comprises an inflatable chamber comprising an upper and lower chamber wall and a second fastener disposed proximate the upper chamber wall, the lower chamber wall being arranged in use, to extend proximate the limb of the wearer. The fastener associated with the first portion is arranged to detachably couple with the fastener associated with the second portion to detachably couple the first and second portions together, by positioning the lower chamber wall of one portion over the upper chamber wall of the other portion.

11 Claims, 5 Drawing Sheets

(58) Field of Classification Search
CPC ........... A61F 13/069; A61F 2005/0183; A61H 2201/1697; A61H 2205/106; A61H 2201/1654; A61H 2205/10; A61H 2205/12; Y10S 128/20; Y10S 2/91; A47G 2009/003; A47G 2009/004; A61G 7/075
USPC .... 602/13, 12, 14, 3, 4, 5, 6, 23, 24, 21, 20, 602/19, 18, 25, 26, 27, 28, 29; 128/845
See application file for complete search history.

(56) References Cited

U.S. PATENT DOCUMENTS

| | | | |
|---|---|---|---|
| 9,119,760 B2 * | 9/2015 | Purdy | A61H 9/0078 |
| 2005/0187503 A1 | 8/2005 | Tordella et al. | |
| 2012/0253250 A1 * | 10/2012 | Spahn | A61F 5/0127 |
| | | | 602/13 |
| 2012/0316481 A1 | 12/2012 | Purdy et al. | |
| 2013/0239976 A1 | 9/2013 | Purdy et al. | |
| 2013/0326789 A1 * | 12/2013 | Lehrman | A41D 19/0034 |
| | | | 2/160 |
| 2014/0135671 A1 | 5/2014 | Spahn et al. | |
| 2015/0088044 A1 * | 3/2015 | Walborn | A61F 5/0111 |
| | | | 602/13 |
| 2016/0255892 A1 * | 9/2016 | Berry | A41F 1/06 |

OTHER PUBLICATIONS

Patents Act 1977: Search Report under Section 17(5), related to Application No. GB1503579.3 dated Jul. 30, 2015, 4 pages.

* cited by examiner

LIMB SUPPORT AND LIMB SUPPORT FASTENING ARRANGEMENT

The present invention relates to a limb support and a limb support fastening arrangement for fastening a limb support to the limb of a wearer.

Inflatable devices supports are currently provided to patients to protect, support and treat parts of the patients body susceptible to the development of pressure sores and ulcers.

The inflatable device is arranged to minimise the development of pressure sores and ulcers by dispersing the weight of the body part across the surface area of the support. Many devices are formed of a polyurethane material to satisfy infection control standards, while also allowing for the devices to be disinfected and reused across multiple patients. However, to date it has proven difficult to secure certain devices to the patient without compromising infection control standards and expectations.

Various fastening arrangements have been tested for securing supports to a patient, including hook and loop (VELCRO ®) fastening straps, buckles and the like. However, it is widely acknowledged that these fastening arrangements can compromise infection control standards. This is because these fastening arrangements do not facilitate a suitable disinfection and cleaning thereof, and also provide an additional surface against which another part of the patients body can rub, thus increasing the risk of developing pressure sores and ulcers on other parts of the body.

According to a first aspect of the present invention, there is provided a limb support fastening arrangement for fastening a limb support to a limb of a wearer, the arrangement comprising a first and second fastening portion, the first portion comprising an inflatable chamber comprising an upper and lower chamber wall and a first fastener disposed proximate the upper chamber wall, the lower chamber wall being arranged in use, to extend proximate the limb of the wearer, the second portion comprising an inflatable chamber comprising an upper and lower chamber wall and a second fastener disposed proximate the upper chamber wall, the lower chamber wall being arranged in use, to extend proximate the limb of the wearer, wherein the fastener associated with the first portion is arranged to detachably couple with the fastener associated with the second portion to detachably couple the first and second portions together, by positioning the lower chamber wall of one portion over the upper chamber wall of the other portion.

The location of the first and second fasteners at the upper side of each portion ensures that the fasteners are held in spaced relation from the limb of the wearer, by virtue of the inflatable chambers, and thus prevents the fasteners from coming into contact or otherwise rubbing against the skin of the wearer of the limb support.

In an embodiment, the chamber of the first and second portion may be arranged in fluid communication.

In an embodiment, the fastening arrangement comprises a plurality of first and second fasteners disposed proximate the upper chamber wall of at least one of the first and second portions, respectively, however, it is envisaged that the first and second portions may separately comprise a plurality of first and second fasteners respectively, disposed proximate the upper chamber wall.

In an embodiment, the plurality of fasteners associated with the first and/or second portion are preferably arranged in spaced relation along the respective portion, and preferably along a longitudinal axis of the respective portion so that the effective length of the fastening arrangement can be varied to accommodate various size limbs, for example.

In an embodiment, the or each magnet is disposed in a corresponding pocket disposed on the upper chamber wall.

In an embodiment, the first and second fasteners comprise magnets.

According to a second aspect of the present invention, there is provided a limb support for supporting the limb of a wearer, the limb support comprising a plurality of inflatable chambers arranged in fluid communication, and a limb support fastening arrangement according to the first aspect, wherein the inflatable chambers of the first and second portions of the fastening arrangement are arranged in fluid communication with the inflatable chambers of the support.

In an embodiment the limb support fastening arrangement is formed integrally with the limb support.

In an embodiment, the support further comprises an adapter for coupling the support to a source of pressurised fluid, for inflating the support.

In an embodiment, the support preferably further comprises at least one window disposed within the inflatable chambers, to permit air to circulate between the inflatable chambers of the support and the limb of the wearer.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

Embodiments of the present invention will now be described by way of example only and with reference to the accompanying drawings in which.

Figure 1:
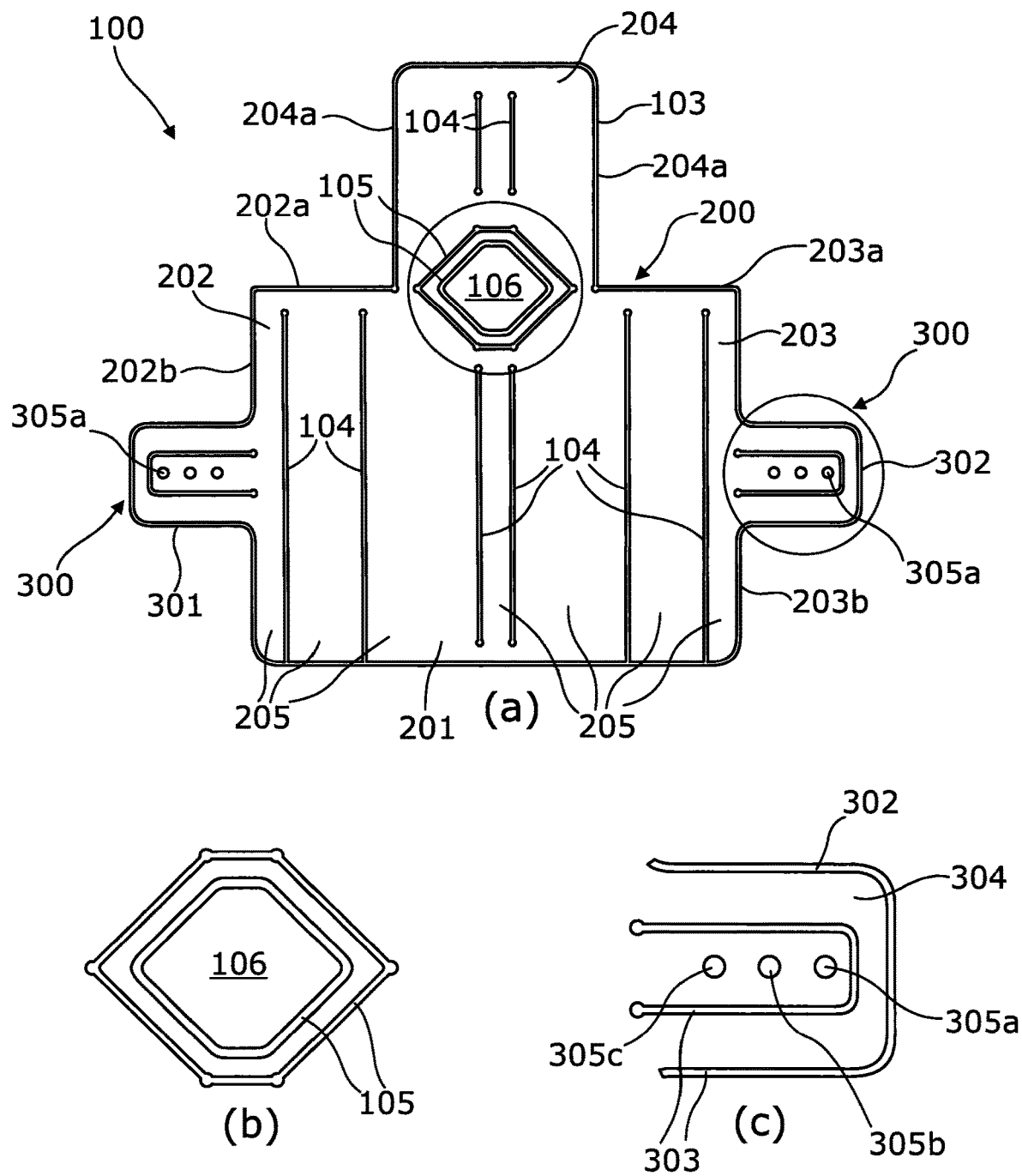
FIG. 1a is schematic illustration of a limb support and limb support fastening arrangement blank.
FIG. 1b is magnified view of the window portion of FIG. 1a, as identified with the circled region A.
FIG. 1c is magnified view of a fastening portion of FIG. 1a, as identified with the circled region B.
Figure 3:
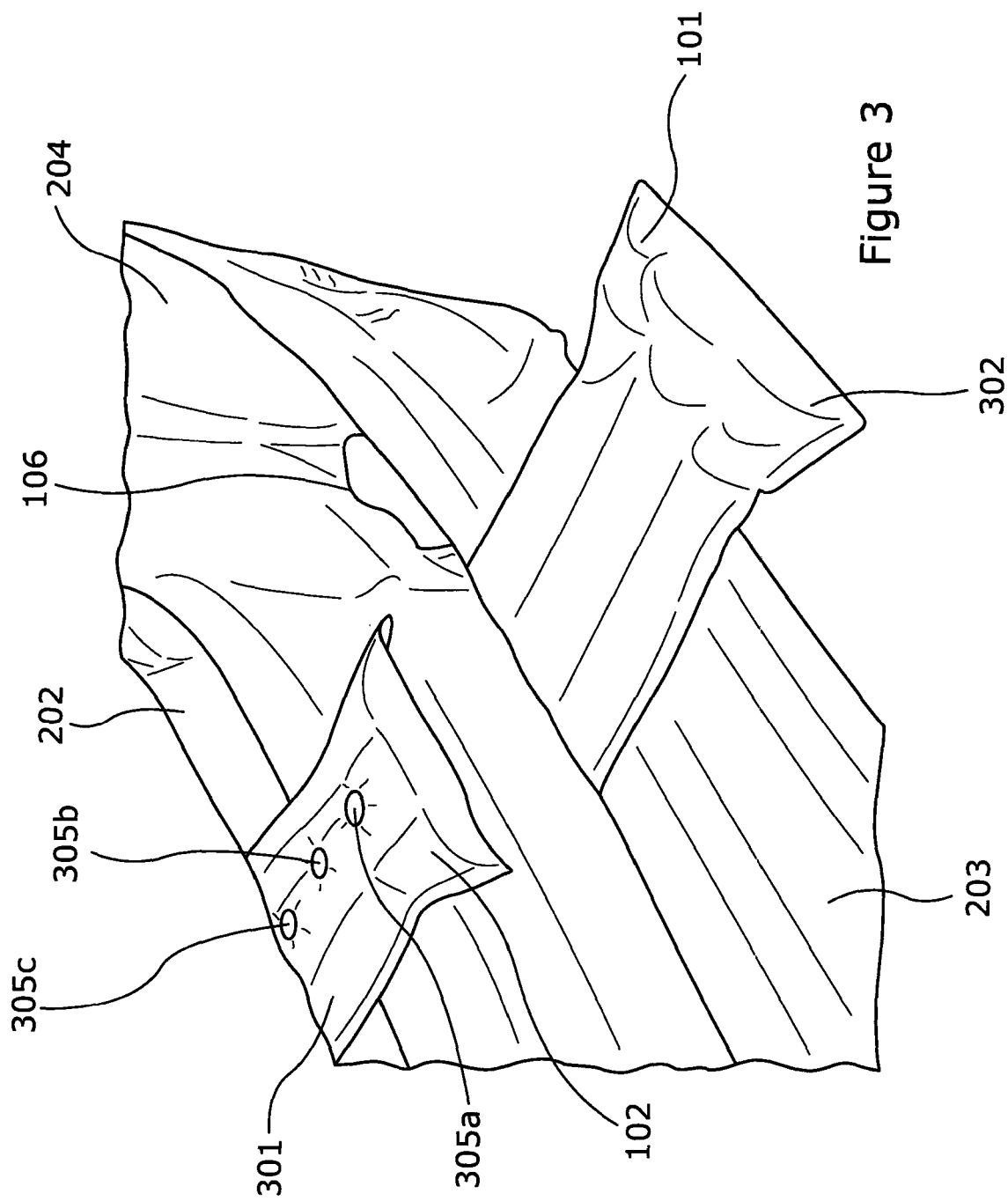
FIG. 3 is a perspective view of a limb support and limb support fastening arrangement according to an embodiment of the present invention, arranged in an inflated configuration with the first and second portions arranged in a partially fastened configuration.

Referring to FIG. 1 of the drawings, there is illustrated an integrally formed limb support and limb support fastening arrangement blank 100 from which a limb support 200 and limb support fastening arrangement 300 according to an embodiment of the present invention, may be constructed. The blank 100 comprises a first and second flexible plastics layer 101, 102, such as polyurethane, with the first layer 101 being disposed upon the second layer 102 (as illustrated in FIG. 3 of the drawings). The layers 101, 102 are ultrasonically welded or otherwise bonded together along a predefined path to form a peripheral region 103 of the limb support 200 and fastening arrangement 300 according to an embodiment of the present invention.

The blank 100 illustrated in FIG. 1 is arranged in use, to form a support 200 for a foot (not shown) of a wearer (i.e. patient), however, the skilled reader will recognise that other blanks may be used for constructing supports for supporting different types of a limb, such as an arm or leg (not shown). The support region of the blank 100 illustrated in FIG. 1 of the drawings comprises a sole portion 201, which is arranged to extend at the underside of the wearers foot, opposing wing portions 202, 203 which in use, are arranged to extend upwardly from a proximal edge thereof which extends along the sole portion 201, along opposite sides of the wearers foot and ankle, and a rear portion 204 which extends along a rear of the sole portion 201, and which in use is arranged to extend around a rear of the wearers foot and ankle. The blank 100 further comprises a limb support fastening arrangement 300 comprising a first and second portion 301, 302, formed integrally with the support 200, which separately extend from a respective wing portion 202, 203 of the limb support 200.

The blank 100 illustrated in FIG. 1, further comprises a plurality of welds 104 arranged in spaced relation across the support 200, which extend partially along the length of the support 200, to bond the first and second layers 101, 102 together and to define a plurality of inflatable chambers 205 arranged in fluid communication with each other. At the intersection of the sole portion 201 with the rear portion 204 there is provided a series of concentric welds 105 which extend around an aperture or window 106 in the blank 100, as illustrated in FIG. 1 b of the drawings. The first and second portions 301, 302 of the fastening arrangement 300 similarly comprise a plurality of welds 303 which extend along the length of the respective portion 301, 302, to define a plurality of respective chambers 304, each of which are arranged in fluid communication with the chambers 205 of the support 200, as illustrated in FIG. 1c of the drawings.

Figure 2:
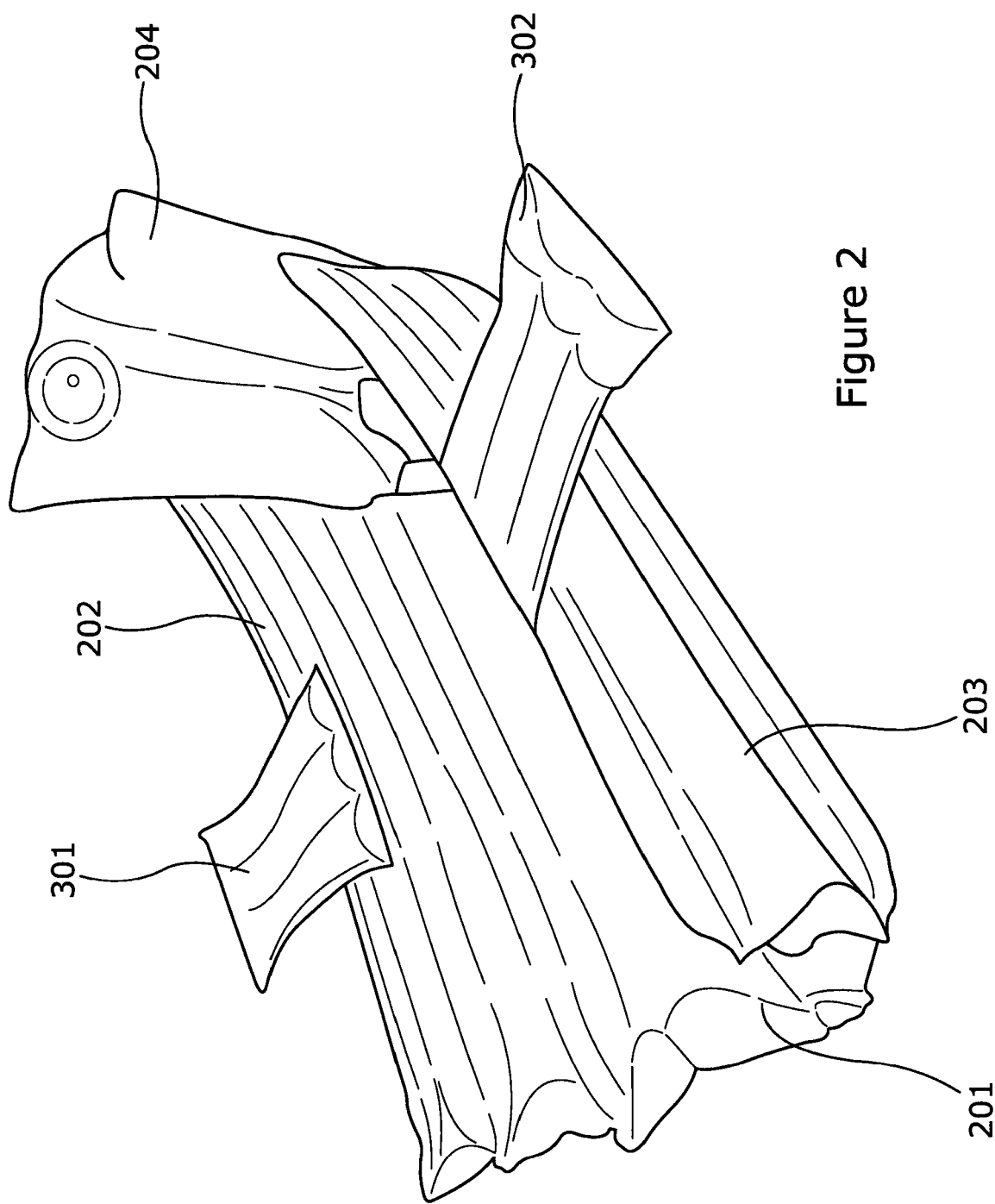
FIG. 2 is a perspective view of a limb support and limb support fastening arrangement according to an embodiment of the present invention, arranged in an inflated configuration with the first and second portions arranged in an unfastened configuration.

The support 200 for the foot is constructed from the blank 100 by further welding or otherwise bonding rearward edges 202a, 203a of the wing portions 202, 203 to the adjacent side edge 204a of the rear portion 204, such that the wing portions 202, 203 and rear portion 204 extend substantially upwardly from the sole portion 201, as illustrated in FIG. 2 of the drawings to define a receptacle for receiving the wearers foot (not shown). The support 200 further comprises an adapter 206 disposed at the rear of the rear portion 204, which is arranged in fluid communication with the chambers 205 of the support 200. The adapter 206 is arranged to couple with a source of pressurised fluid, such as a pump or similar (not shown), for introducing a fluid, such as air, between the first and second layers 101, 102, to inflate the chambers 205 of the support 200 and the chambers 304 of the first and second portions 301, 302 of the fastening arrangement 300.

Figure 4:
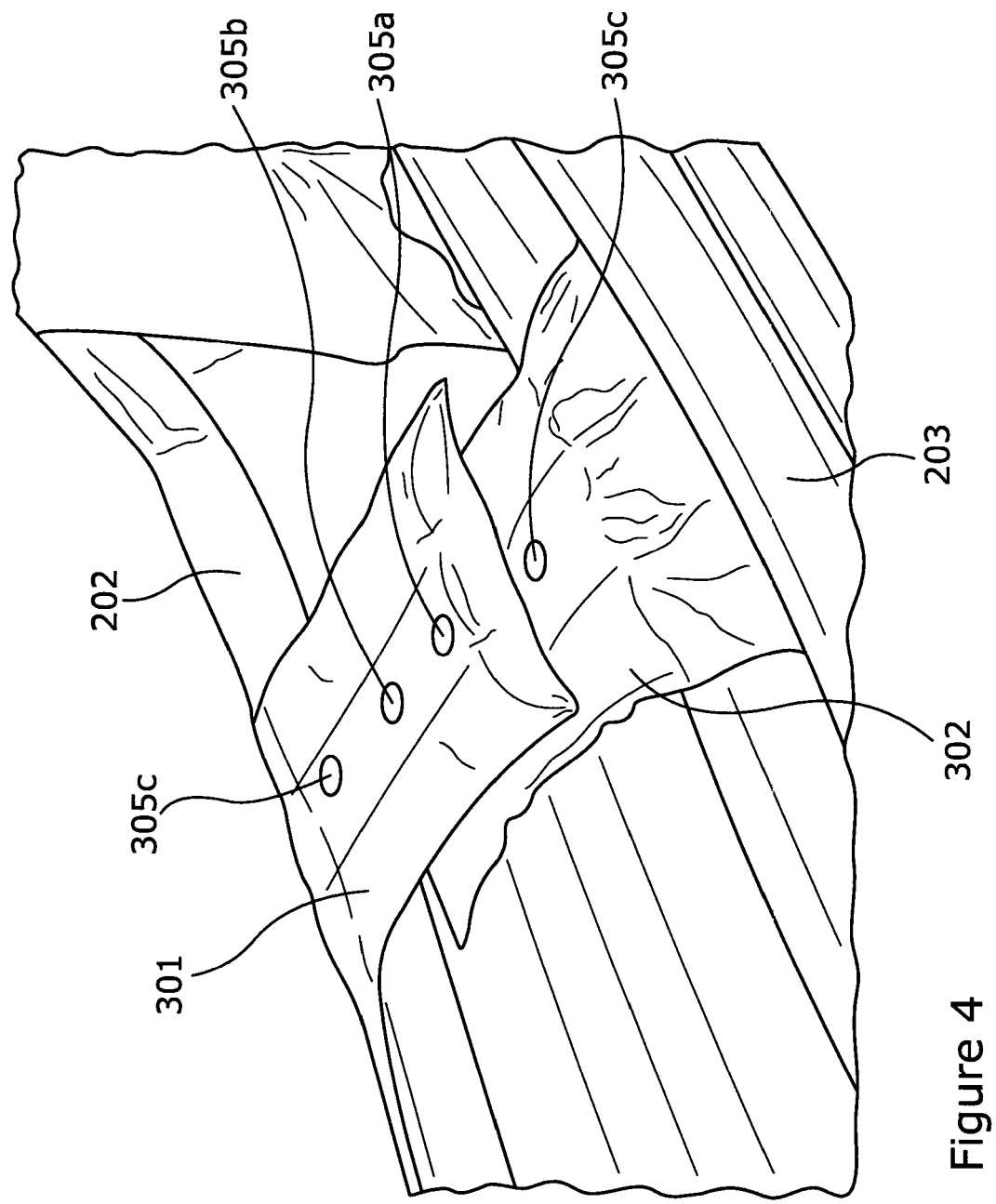
FIG. 4 is a perspective view of a limb support and limb support fastening arrangement according to an embodiment of the present invention, arranged in an inflated configuration with the first and second portions arranged in a fastened configuration; and, FIG. 5 is a perspective rear view of a limb support and limb fastening arrangement according to an embodiment of the present invention.
Figure 5:
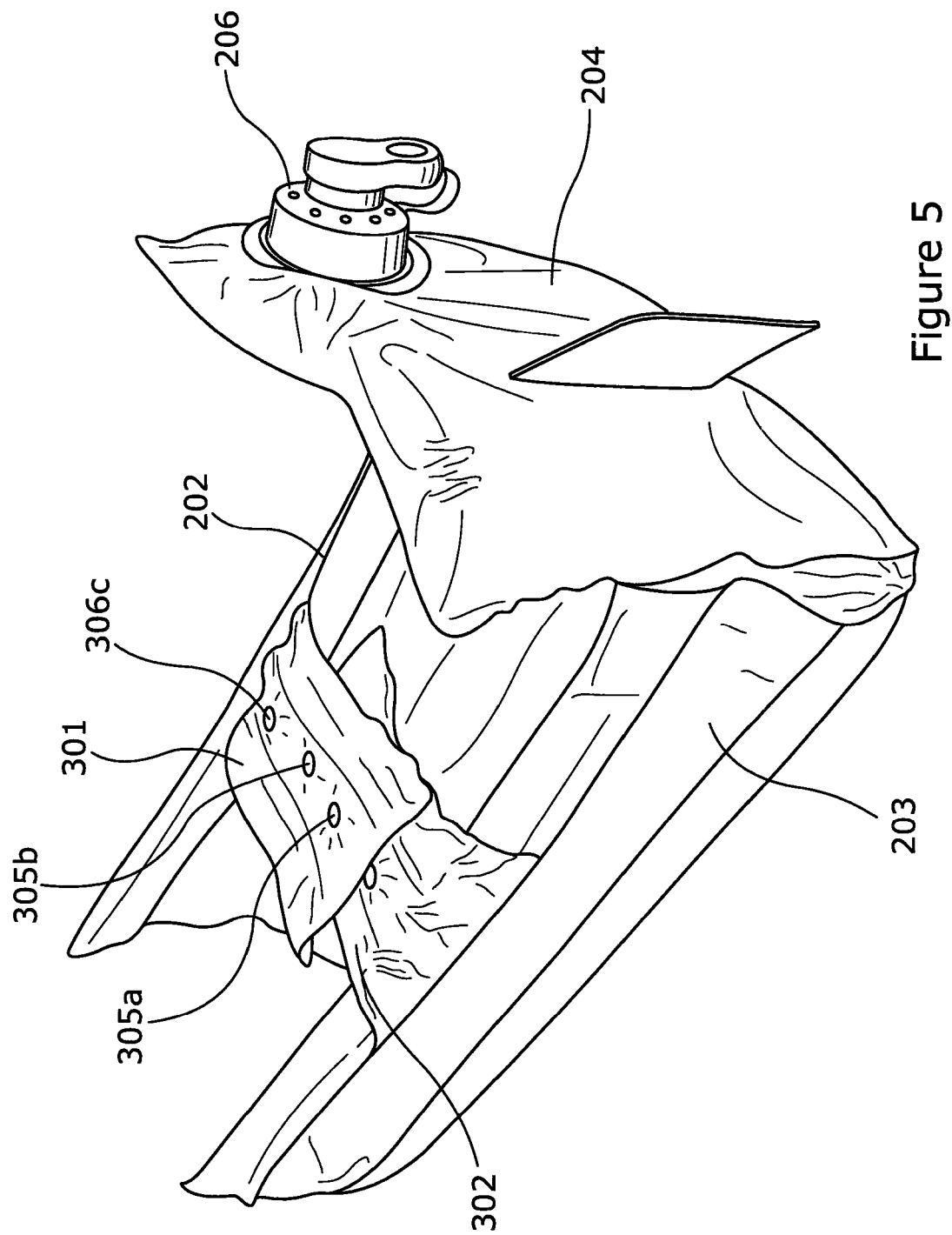

In use, with the support 200 arranged in an inflated condition, the first and second portions 301, 302 of the fastening arrangement 300 extend from a distal edge 202b, 203b of a respective wing portion 202, 203 and are reconfigurable between a first configuration in which the portions 301, 302 separately extend outwardly of the support 200, away from the adjacent wing portion 203, 202, as illustrated in FIG. 2 of the drawings and a second configuration in which the first and second portions 301, 302 separately extend toward the adjacent wing portion 203, 202, over the sole portion 201, as illustrated in FIG. 4 of the drawings.

The first and second portions 301, 302 comprise a respective first and second fastener, which permit a detachable coupling of the first and second portions. The first and second fasteners may comprise a first and second interlocking disc forming a press stud (not shown), or a first and second magnet 305, for example. The first and second fasteners are disposed proximate the second layer 102, which is arranged to form the upper layer of the chambers 304 of the first and second portion 301, 302 when the portions 301, 302 are arranged in the second configuration. In the embodiment illustrated in FIGS. 2-5 of the drawings, the first and second portions 301, 302 of the fastening arrangement 300 separately comprise three magnets 305a-c (illustrated most clearly in FIGS. 3 and 4 of the drawings) arranged in spaced relation along a longitudinal axis of the respective portion 301, 302. The spaced relation of the magnets 305a-c along each portion 301, 302 enables the relative overlap of the first and second portions 301, 302 to be varied, while still ensuring a suitable coupling of the first and second portions 301, 302. The ability to vary the overlap provides for a range of different limb, namely feet sizes which can be suitably accommodated within the support 200.

The fasteners, such as the magnets 305a-c, are separately located within a respective pocket (not shown) formed on the second layer 102 and are thus held separated from the first layer 101, which is arranged to form the lower layer of the chambers 304 of the first and second portion 301, 302 when the portions 301, 302 are arranged in the second configuration. In use, the foot support 200 is inflated by coupling a source of pressurised fluid (not shown) to the adapter 206 so that the fluid, such as air, can permeate between the first and second layer 101, 102 and inflate the chambers 205 of the support 200 and the chambers 304 of the first and second portion 301, 302 of the fastening arrangement 300. As the chambers 304 of the first and second portion 301, 302 become inflated, the magnets 305a-c disposed on the second layer 102 become separated from the first layer 101 by the air disposed therein.

A wearer subsequently places their foot (not shown) within the support 200, so that the underside of the wearers foot extends upon the sole portion 201 and the wearers heal extends proximate the window 106. The window 106 enables air to circulate into the support 200, between the first layer 101 and the wearer's foot and helps maintain a suitable temperature within the support 200. The ventilation window 106 further helps minimise the development of pressure sores, for example and further permits an inspection of the limb without requiring the removal of the support 200.

To secure the support 200 to the wearer's foot, either of the first or second portion 301, 302 of the fastening arrangement 300, for example the first portion 301, is reconfigured to the second configuration over the wearers foot, and the other of the first or second portion 301, 302, for example the second portion 302, is subsequently passed over the first portion 301. The relative overlap of the first and second portion 301, 302 determines which of the fasteners, for example the magnets 305a-c within the first and second portions 301, 302 become involved in fastening the portions 301, 302 together. For example, a small overlap will only result in the magnet 305a disposed proximate the free end of each portion 301, 302 becoming coupled together. However, as the relative overlap increases, the further magnets 305b-c will become involved in fastening the portions 301, 302.

As the magnets 305a-c of one portion 301 couple with the magnets 305a-c of the other portion 302, the chamber disposed in the uppermost portion of the fastened arrangement become compressed owing to the attraction of the magnets 305a-c. This acts to increase the pressure slightly within the support 200 to further improve the fit of the support 200 upon the wearer's foot. Similarly, in the embodiment where the fasteners comprise press studs (not shown), the chamber disposed in uppermost portion 302 of the fastened arrangement becomes compressed as the discs associated with the studs couple together. It is to be appreciated, that in this embodiment the upper 101 layer of the lowermost portion 301 and lower layer 102 of the uppermost portion 302 becoming secured between the discs forming the press stud (not shown). However, regardless of whether the first portion 301 is positioned over the second portion 302 or whether the second portion 302 is positioned over the first portion 301, the location of the fasteners, such as the magnets 305a-c upon the second layer 102, namely at the upper side of the portions 301, 302 when configured overt the wearer's foot, ensures that the magnets 305a-c are held separated from the wearers foot by virtue of the inflated chamber or chambers 304 of the lowermost portion, and thus minimise any sores developing upon the wearers foot. Moreover, the sealed nature of the chambers 205, 304 and the magnets 305a-c within the pockets (not shown) facilitates a suitable disinfection and cleaning of the support and fastening arrangement, for subsequent use.

The invention claimed is:

1. A limb support fastening arrangement for fastening a limb support to a limb of a wearer, the arrangement comprising: a first and second layer, the first layer being disposed upon the second layer, the layers being bonded togetherto define a first wing portion; a second wing portion; a first fastening portion extending outwardly away from the first wing portion; and a second fastening portion extending outwardly away from the second wing portion,
the first fastening portion comprising an inflatable chamber defined between the first and second layers, and a first fastener on the second layer, the first layer being arranged, in use, to form an inner layer of the first fastening portion, such that the first layer of the first fastening portion is proximal the limb of the wearer, the second layer being arranged, in use, to form an outer layer of the first fastening portion, such that the second layer of the first fastening portion is distal to the limb of the wearer,
the second fastening portion comprising an inflatable chamber defined between the first and second layers, and a second fastener on the second layer, the first layer being arranged, in use, to form an inner layer of the second fastening portion, such that the first layer of the second fastening portion is proximal to the limb of the wearer and the second layer being arranged, in use, to form an outer layer of the second fastening portion, such that the second layer of the second fastening portion is distal to the limb of the wearer,
wherein each of the first fastener and the second fastener is disposed in a corresponding pocket disposed on the second layer of the respective first and second fastening portions and the first fastener is arranged to detachably couple with the second fastener to detachably couple the first fastening portion and the second fastening portion together, by contacting the first layer of the first/second fastening portion on top of the second layer of the second/first fastening portion thus preventing the first fastener and the second fastener from coming into contact with skin of the wearer of the limb support by virtue of the inflatable chamber.

2. The limb support fastening arrangement according to claim 1, wherein the first and second fasteners comprise a plurality of first and second fasteners disposed proximate the second layer of at least one of the first and second fastening portions, respectively.

3. The limb support fastening arrangement according to claim 2, wherein the plurality of first fasteners associated with the first fastening portion are arranged in spaced relation along the first fastening portion and the plurality of second fasteners associated with the second fastening portion are arranged in spaced relation along the second fastening portion.

4. The limb support fastening arrangement according to claim 3, wherein the plurality of first fasteners are arranged in spaced relation along a longitudinal axis of the first fastening portion and the plurality of second fasteners are arranged in spaced relation along a longitudinal axis of the second fastening portion.

5. A limb support for supporting the limb of a wearer, the limb support comprising a plurality of inflatable chambers arranged in fluid communication, and a limb support fastening arrangement according to claim 1, wherein the inflatable chambers of the first and second fastening portions of the fastening arrangement are arranged in fluid communication with the plurality of inflatable chambers of the limb support.

6. The limb support according to claim 5, wherein the limb support fastening arrangement is formed integrally with the limb support.

7. The limb support according to claim 5, further comprising an adapter for coupling the limb support to a source of pressurised fluid, for inflating the limb support.

8. The limb support fastening arrangement according to claim 1, wherein the chambers of the first and second fastening portions are arranged in fluid communication.

9. The limb support fastening arrangement according to claim 1, wherein the first and second fasteners comprise a plurality of first and second fasteners disposed proximate the second layer of the first and second fastening portions, respectively.

10. The limb support fastening arrangement according to claim 1, wherein the first and second fasteners comprise magnets.

11. The limb support fastening arrangement according to claim 1, wherein the inflatable chamber of the first fastening portion or the second fastening portion which overlaps the second fastening portion or the first fastening portion, respectively, becomes compressed when the first and second fasteners are coupled together.

* * * * *